United States Patent
King et al.

(10) Patent No.: US 10,399,064 B2
(45) Date of Patent: Sep. 3, 2019

(54) RHENIUM RECOVERY FROM USED REDUCTIVE AMINATION CATALYSTS

(71) Applicant: DOW Global Technologies LLC, Midland, MI (US)

(72) Inventors: Stephen W. King, League City, TX (US); William C. Hoffman, Decatur, IL (US)

(73) Assignee: DOW Global Technologies LLC, Midland, MI (US)

(*) Notice: Subject to any disclaimer, the term of this patent is extended or adjusted under 35 U.S.C. 154(b) by 0 days.

(21) Appl. No.: 14/387,101

(22) PCT Filed: Mar. 11, 2013

(86) PCT No.: PCT/US2013/030233
§ 371 (c)(1),
(2) Date: Sep. 22, 2014

(87) PCT Pub. No.: WO2013/148140
PCT Pub. Date: Oct. 3, 2013

(65) Prior Publication Data
US 2015/0087837 A1    Mar. 26, 2015

Related U.S. Application Data

(60) Provisional application No. 61/616,236, filed on Mar. 27, 2012.

(51) Int. Cl.
| | | |
|---|---|---|
| *C01G 47/00* | (2006.01) | |
| *B01J 23/889* | (2006.01) | |
| *C22B 7/00* | (2006.01) | |
| *C22B 61/00* | (2006.01) | |
| *B01J 38/58* | (2006.01) | |
| *B01J 38/70* | (2006.01) | |
| *B01J 23/94* | (2006.01) | |
| *B01J 23/92* | (2006.01) | |
| *B01J 37/02* | (2006.01) | |
| *C07C 209/16* | (2006.01) | |
| *C07C 213/02* | (2006.01) | |
| *C07D 295/027* | (2006.01) | |
| *B01J 38/12* | (2006.01) | |
| *B01J 38/60* | (2006.01) | |
| *B01J 38/64* | (2006.01) | |

(52) U.S. Cl.
CPC ......... *B01J 23/8896* (2013.01); *B01J 23/92* (2013.01); *B01J 23/94* (2013.01); *B01J 37/0201* (2013.01); *B01J 38/58* (2013.01); *B01J 38/70* (2013.01); *C07C 209/16* (2013.01); *C07C 213/02* (2013.01); *C07D 295/027* (2013.01); *C22B 7/009* (2013.01); *C22B 61/00* (2013.01); *B01J 38/12* (2013.01); *B01J 38/60* (2013.01); *B01J 38/64* (2013.01); *Y02P 10/214* (2015.11); *Y02P 20/584* (2015.11)

(58) Field of Classification Search
None
See application file for complete search history.

(56) References Cited

U.S. PATENT DOCUMENTS

| | | | |
|---|---|---|---|
| 3,578,395 A | | 5/1971 | Kluksdahl et al. |
| 4,585,618 A | * | 4/1986 | Fresnel ............ C04B 35/65 204/242 |
| 6,534,441 B1 | * | 3/2003 | Bartley ............ B01J 23/8896 502/241 |
| 7,704,908 B2 | | 4/2010 | Matusz et al. |
| 7,763,096 B2 | | 7/2010 | Rizkalla et al. |
| 2003/0119658 A1 | | 6/2003 | Allison et al. |
| 2005/0095189 A1 | | 5/2005 | Brey et al. |
| 2009/0148361 A1 | | 6/2009 | Herman et al. |
| 2010/0087681 A1 | * | 4/2010 | Petraitis ............ C07C 209/08 564/470 |
| 2010/0087682 A1 | | 4/2010 | King et al. |
| 2010/0137642 A1 | | 6/2010 | King et al. |

FOREIGN PATENT DOCUMENTS

| | | | | |
|---|---|---|---|---|
| CN | 1165712 A | * | 11/1997 | ............ B01J 38/02 |
| EP | 0 568 407 | | 11/1993 | |
| EP | 0 930 346 | | 7/1999 | |
| EP | 1 749 566 | | 2/2007 | |
| GB | 1 282 116 | | 7/1972 | |

OTHER PUBLICATIONS

CN 1165712 A translation.*
Millensifer, T. A. 2010. Rhenium and Rhenium Compounds. Kirk-Othmer Encyclopedia of Chemical Technology. 1-22.

* cited by examiner

*Primary Examiner* — Yun Qian
(74) *Attorney, Agent, or Firm* — Kagan Binder PLLC

(57) ABSTRACT

The present invention provides techniques that selectively recover Re from reductive amination catalysts. In particular, the present invention allows Re to be recovered selectively relative to Ni, Co, and/or Cu, and particularly Ni, that are often present on reductive amination catalysts. The present invention uses a combination of oxidation and extraction techniques to selectively recover Re relative to Ni, Co, and/or Cu. Advantageously, the recovery is selective even when using aqueous solutions for extraction.

18 Claims, No Drawings

RHENIUM RECOVERY FROM USED REDUCTIVE AMINATION CATALYSTS

PRIORITY

The present application claim priority to International Application No. PCT/US2013/030233, filed Mar. 11, 2014, which in turns claims priority under 35 USC § 119(e) from U.S. Provisional Patent Application having Ser. No. 61/616,236, filed Mar. 27, 2012 entitled "RHENIUM RECOVERY FROM USED REDUCTIVE AMINATION CATALYSTS," wherein the disclosures of these applications are incorporated herein by reference in their respective entireties for all purposes.

FIELD OF THE INVENTION

The present invention relates to the selective recovery of rhenium from used heterogeneous catalysts after using the catalysts for reductive amination in a reducing environment. More particularly, the present invention relates to such recovery where the catalyst includes Re and at least one of Ni, Co, and/or Cu.

BACKGROUND OF THE INVENTION

Reductive amination is an important commercial process in which reactants such as alcohols, ketones, aldehydes, or the like are converted to amines. The reactants form imine intermediate(s). These are then reduced to form amine products. For instance, reductive amination techniques can be used to react monoethanolamine (MEA) and ammonia to form amine reaction products.

Reductive amination generally is carried out in the presence of a catalyst in a reducing environment. A typical catalyst includes at least one catalytically active metal having an activity for reductive amination. Examples of such metals include Ni, Co, and/or Cu. Rhenium (Re) is also incorporated into these catalysts. Although Re may have catalytic activity on its own, it is believed that Re functions as a promoter to enhance the catalytic activity of the Ni, Co, and/or Cu.

Fresh catalyst has a certain level of activity and selectivity for catalyzing reductive amination. The selectivity and/or activity may diminish over time as the catalyst ages and is used. At some point, the catalyst is deemed to be spent and is replaced. Other times, the catalyst may still have activity and selectivity, but the manufacturing plans have changed so that the catalyst is no longer needed.

To be effective for reductive amination, catalysts incorporate relatively large amounts of Re. For example, weight loadings greater than 0.5 weight percent Re on a metals basis based on the total weight of the catalyst typically are used. Thus, a significant amount of Re is used to carry out reductive amination on a commercial scale. Other kinds of catalysis use much less Re under different conditions. For instance, ethylene oxide (EO) catalysis uses much lower amounts of Re, the catalysis occurs in an oxidizing environment, and the catalyst often includes significant amounts of Ag. Thus, in a typical recovery of Re from EO catalysts, the catalyst was used in an oxidizing environment, and the Re is to be recovered selectively relative to substantial amounts of Ag.

Rhenium also is an extremely expensive and rare metal. Rhenium costs have gone as high as $10,000 per kg. Based on the amount of Re being used and its cost, it is highly desirable to recover and re-use Re from spent catalysts. More particularly, it is desirable to recover Re selectively relative to other catalyst constituents to avoid undue contamination and thereby simplify recycling of Re.

Extraction techniques have been used to recover Re from spent catalysts. Unfortunately, U.S. Pat. No. 7,763,096 reports that aqueous extraction has poor selectivity for Re. Significant amounts of other catalyst constituents are extracted along with the Re so that the Re is contaminated with these other materials. US 2009/0148361 also reports that aqueous extraction can recover both Re and metal catalysts non-selectively and thereby hinder or complicate recovery of the Re.

There remains a strong need to selectively recover Re from used reductive amination catalysts. In particular, there is a strong need to recover Re selectively relative to Ni, Co, and/or Cu from used reductive amination catalysts

SUMMARY OF THE INVENTION

The present invention advantageously provides techniques that selectively recover Re from reductive amination catalysts. In particular, the present invention allows Re to be recovered selectively relative to Ni, Co, and/or Cu, and particularly Ni, that are often present on reductive amination catalysts. The recovered Re can then be recycled for use in any desired application that uses Re. In particular, the recovered Re can be used to prepare new reductive amination catalysts. The recovered Re is also useful in other catalyst applications, e.g., ethylene oxide catalysis, hydrocarbon processing, gasoline processing, catalytic reforming, and the like. The recovered Re may also be incorporated into Re-containing alloys and used in high tech applications such as being used as an additive in Ni-based superalloys.

The present invention uses a combination of oxidation and extraction techniques to selectively recover Re relative to Ni, Co, and/or Cu from a substrate that comprises a threshold amount of alumina optionally with silica also being present. The use of a substrate with a threshold amount of alumina provides numerous advantages when recovering Re from a reductive amination catalyst. First, it has been found that the catalyst substrate is more robust to reductive amination with increasing alumina content. In particular, alumina helps to provide the substrate with greater resistance to powdering under reductive amination conditions. This helps to preserve the integrity of the catalyst to facilitate recovery of Re from the catalyst. In contrast, less robust substrates have a substantially greater tendency to powder or otherwise degrade, making Re recovery substantially more difficult.

Advantageously, the recovery of Re according to the present invention is selective even when using aqueous solutions for extraction. Oxidation is believed to convert the Re into a form that is more soluble in water and polar organic solvents. But, what also is surprising is that the selectivity also is improved with respect to Ni, Co, and/or Cu. Conventional experience suggests that mere oxidation improves solubility but not selectivity. Without wishing to be bound by theory, it is believed that the use of the catalysts in a reducing environment to carry out reductive amination and the nature of the reductive amination catalysts contribute to the selectivity that is observed when the Re is oxidized for extraction. The present invention appreciates, therefore, that the environment in which a catalyst is used can impact the later selective recovery of Re from the catalyst. Without wishing to be bound by theory, it also is believed that the alumina content of the substrate further promotes this selectivity in that Ni and other catalytically active species may tend to be more strongly bound to alumina than is the Re. Consequently, the oxidized Re is more easily extracted from the catalyst than Ni and possibly other species as well.

In one aspect, the present invention relates to a method for recovering rhenium from a reductive amination catalyst, comprising the steps of:
  a) providing a heterogeneous catalyst that has been used in a reducing atmosphere to carry out a reductive amination, wherein the catalyst comprises a substrate and at least one species comprising rhenium and at least one species comprising nickel supported on the substrate, wherein the at least one species comprising rhenium has a first solubility in a liquid carrier and wherein the substrate comprises at least 15 weight percent alumina based on the total weight of the substrate;
  b) causing the catalyst to contact the liquid carrier in the presence of heat and at least one oxidizing agent under conditions effective to convert at least a portion of the Re-containing species into a Re-containing product that has a second solubility in the liquid carrier, wherein the second solubility is greater than the first solubility; and
  c) extracting the Re-containing product into the liquid carrier.

In another aspect, the present invention relates to a method of making a heterogeneous catalyst, comprising the steps of:
  a) providing a catalyst that has been used in a reducing atmosphere to carry out a reductive amination, wherein the catalyst comprises a substrate and at least one species comprising rhenium in an oxidation state less than 7+ and at least one species comprising nickel supported on the substrate, and wherein the substrate comprises at least 15 weight percent alumina based on the total weight of the substrate;
  b) causing the catalyst to contact a liquid in the presence of heat and at least one oxidizing agent under conditions effective to extract a Re-containing species into the liquid, said extracted Re-containing species comprising Re in an oxidation state of 7+;
  c) using the liquid comprising the extracted Re-containing species to prepare an impregnation solution comprising the extracted Re-containing species;
  d) using the impregnation solution to prepare a heterogeneous catalyst comprising a Re-containing species and a Ni-containing species, said Re-containing species comprising Re, wherein at least a portion of the Re in the Re-containing species is in an oxidation state of 7+; and
  e) optionally treating the heterogeneous catalyst in a reducing atmosphere to provide the catalyst with a catalytic activity for reductive amination.

In another aspect, the present invention relates to a method of using Re in heterogeneous catalysts that have a catalytic activity for reductive amination, comprising the steps of:
  a) providing a first heterogeneous catalyst that comprises a substrate and at least one species containing rhenium in an oxidation state less than 7+ supported on the substrate and at least one species containing catalytically active nickel supported on the substrate, and wherein the substrate comprises at least 15 weight percent alumina based on the total weight of the substrate;
  b) using the first heterogeneous catalyst in a reducing atmosphere to carry out a reductive amination process;
  c) causing the used, first heterogeneous catalyst to contact a liquid in the presence of heat and at least one oxidizing agent under conditions effective to convert at least a portion of the Re-containing species containing rhenium in an oxidation state less than 7+ into an oxidized Re-containing product that comprises Re in an oxidation state of 7+ and under conditions such that the oxidized Re-containing product is extracted into the liquid;
  d) causing ingredients comprising the oxidized Re-containing product to be used to prepare a second heterogeneous catalyst that has a catalytic activity for reductive amination in a reducing atmosphere; and
  e) causing the second heterogeneous catalyst to be used in a reducing atmosphere for reductive amination.

DETAILED DESCRIPTION

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

The present invention is directed to a process for selectively recovering rhenium from a heterogeneous catalyst after the heterogeneous catalyst has been used in a reductive amination process in a reducing environment. The rhenium may function in any suitable manner, including, for example, as a catalytically active species and/or promoter. In a particular embodiment, the rhenium-containing catalyst is a reductive amination catalyst that contains at least one of Ni, Co, and/or Cu as a catalytically active species on a solid support.

The heterogeneous catalyst may be provided for Re recovery at any time after it has been used in a reductive amination process carried out in a reducing atmosphere. For example, the catalyst may be provided for Re recovery after the catalyst has aged and become spent to some degree. As used herein, a catalyst is spent if the used and/or aged catalyst has lost a desired level of activity and/or selectivity with respect to use in the desired reductive amination process. For example, a catalyst may be considered spent in some embodiments if the selectivity of the catalyst has dropped by more than 3% compared to the fresh catalyst. More typically, the catalyst is considered spent if the selectivity has dropped by more than 5%. As another example, a catalyst can be considered spent if it is necessary to increase the reaction temperature by more than 3° C., preferably more than 5° C. to maintain desired productivity as originally provided by the fresh catalyst. Having to increase the temperature in this way indicates that the catalyst activity is diminished.

Alternatively, Re recovery can be practiced for a wide variety of other reasons even if the catalyst is not spent to any significant degree. For example, Re recovery may be desirable if a process is decommissioned due to a change in formulation or change in manufacturing plans. Re recovery may also be practiced, for example, if a process is temporarily stopped for maintenance, service, or repair of process facilities. Once recovered, the Re can be used in a variety of ways. For instance, the recovered Re may be sold, stored, or recycled as a component of a fresh catalyst to be used in a reductive amination or other process.

In the practice of the present invention, a heterogeneous catalyst refers to a catalyst for which the phase of the catalyst differs from the phase of at least a portion of the reactants whose reaction is being facilitated by the catalyst. Desirably, heterogeneous catalysts comprise one or more catalytically active materials supported upon a suitable, solid substrate. The substrate may have various shapes or combinations such as, for example, powder, particle, pellet, granule, extrudate, fiber, shell, honeycomb, membrane, cloth, plate, or the like. The particles can be regular in shape, irregular, dendritic, dendrite-free, rounded, square, tetrahedral, or the like. Preferred supports are particulate in nature.

Particulate substrates may have a so-called guest/host structure, which may be prepared by adsorbing or adhering fine (less than 100 micrometers, preferably less than 50 micrometers and most preferably less than 10 micrometer in size) particles on coarser (greater than 30 mesh) particles. The smaller particles are referred to as guests, while the large particles supporting them are referred to as hosts. This small-particle-supported-on-a-larger-particle composite structure provides very high total exterior surface area while retaining the desirable gas passing characteristics, i.e., low pressure drop, of a coarser particle. In addition, by using smaller particles in constructing these composite particles, inexpensive, coarser particles can be used. Thus, very inexpensive, highly active catalyst particles can be prepared since the bulk of the volume of a catalyst bed may be taken up by the inexpensive, underlying, coarser particles. Desirably, the guest/host structures are stable in the reaction environment for a suitable period of time to avoid having to replenish the catalyst with undue frequency.

When catalytically active material is supported on only the guest particles and not the host particles, the threshold alumina content of the present invention desirably applies to the guest particles and optionally to the host particles. Similarly, if the substrate has a core/shell structure in which catalytically active material is provided only on or in a shell portion of the substrate, the threshold alumina content of the present invention desirably applies to the shell portion and optionally to the core portion.

The catalytically active material can be incorporated into or onto the guest and/or host particles. Often, the catalytically active material is incorporated mainly onto the guest material before or after the guest/host composite is formed. Guest/host structures and methods of making these are further described in U.S. Publication No. 2005/0095189 A1.

Optionally, the catalyst support is calcined and reduced prior to use. Calcining may occur at any time during catalyst manufacture such as before and/or after active materials are provided on the support. Generally, calcining can occur in air or an inert atmosphere such as one based upon nitrogen, argon, carbon dioxide, combinations of these, and the like. Calcining can occur at a variety of elevated temperatures, such as a temperature up to about 1000° C., preferably about 200° C. to about 800° C. Reduction with hydrogen or a mixture of hydrogen and an inert (e.g., nitrogen) can occur at a variety of elevated temperatures, such as a temperature up to about 1000° C. preferably about 250-500° C.

In the practice of the present invention, the substrate desirably includes at least a threshold amount of alumina. Without wishing to be bound by theory, it is believed that this features helps the substrate to be more robust to reductive amination conditions. It is also believed this feature helps promote favorable selectivity for extracting oxidized Re from the substrate relative to species including catalytically active Ni. In preferred embodiments, the substrate includes at least 15 weight percent, preferably at least 30 weight percent, more preferably at least 45 weight percent, even more preferably at least 60 weight percent, and even more preferably at least 75 weight percent alumina based on the total weight of the substrate.

The alumina may be present in one or more different phases and/or morphologies. For example, the alumina may be amorphous and/or crystalline. Crystalline phases are preferred. Additionally, the alumina may be present in one or more of α-, β-, γ-, δ-, η-, θ-, and/or χ-phases. The transitional aluminas (δ-, η-, θ-, and/or χ-) are preferred. Corundum is a crystalline form of alumina that may include minor amounts of other constituents such as Fe, Ti, and/or Cr.

In addition to alumina, the substrate may include a wide variety of other materials. Representative examples include inorganic and/or organic materials such as one or more polymers, carbonaceous materials, pumice, silicaceous materials (such as silica), metal-containing species such as metal oxides, metal nitrides, metal carbides, metal carbonates, combinations of these, and the like. Representative metal oxides include oxides of one or more of magnesium, titanium, vanadium, chromium, manganese, iron, cobalt, nickel, copper, zinc, gallium, germanium, strontium, yttrium, zirconium, niobium, molybdenum, technetium, ruthenium, rhodium, palladium, silver, cadmium, indium, iron, tin, antimony, barium, lanthanum, hafnium, thallium, tungsten, rhenium, osmium, iridium, silicon, silver, gold, titanium, and/or platinum.

Examples of suitable metal containing species suitable as all or a portion of a substrate in combination with alumina include magnesia, zirconia, titania, kieselguhr, fuller's earth, silicon carbide, silica, silicon nitride, one or more clays, artificial zeolites, natural zeolites, silicon dioxide, titanium dioxide, other ceramics and/or glasses, and combinations thereof. In many embodiments, the support includes a threshold amount of alumina as described herein and silica. Desirably, the weight ratio of alumina to silica is in the range from about 1:1 to 50:1, preferably 1.5:1 to 20:1, even more preferably from about 2:1 to 8:1. On exemplary embodiment of a substrate includes 80 parts by weight of alumina per about 20 parts by weight of silica. Minor amounts (e.g., less than 10 parts by weight, even less than 5 parts by weight, or even less than 1 part by weight of each such constituent per 80 parts by weight of alumina) of other constituents may be present in such embodiments. Preferred embodiments of inorganic, particulate supports are described in Assignee's co-pending U.S. Published Patent Application 2010/0087682, titled "LOW METAL CATALYST COMPOSITIONS INCLUDING ACIDIC MIXED METAL OXIDE AS SUPPORT" by Stephen W. King et al. Additional inorganic substrates suitable in the practice of the invention also are described in Assignee's co-pending U.S. Published Patent Application 2010/0137642 A1 titled "LOW METAL LOADED, ALUMINA SUPPORTED, CATALYST COMPOSITIONS AND AMINATION PROCESS" by Stephen W. King et al.

Examples of carbonaceous substances in combination with alumina include activated carbon and graphite. Suitable activated carbon particles may be derived from a wide variety of source(s) including coal, coconut, peat, any activated carbon(s) from any source(s), combinations of at least two of these, and/or the like.

Substrates often have a topography to provide high surface area for supporting catalytically active material and other catalyst components such as promoters. Such topography can be provided by texture, folds, loops, strands, porosity, or the like. Particulate substrate embodiments often have a combination of macroporosity, nanoporosity, microporosity, mesoporosity, and/or the like to provide high surface area. In many embodiments, the surface topography is effective to provide the substrate with a BET specific surface area of at least 50 m²/g, often 100 m²/g to 1500 m²/g.

Catalytically active material and other catalyst components such as promoters may be incorporated into heterogeneous catalyst systems in a variety of ways. Exemplary procedures are well known in the industry and include solution impregnation, precipitation, vapor deposition such as by physical or chemical vapor deposition techniques, and the like. In some instances, precursor(s) are first provided on the support, and then the precursor(s) can be converted into the desired ingredient in situ on the substrate.

The heterogeneous catalyst comprises at least one catalytically active species having an activity for reductive amination in a reducing environment. At least one catalytically active species includes at least one of Ni, Co, and/or Cu. Preferably, the at least one catalytically active species includes Ni. The Ni containing species desirably is used in combination with at least one other catalytically active species including at least one of Co and/or Cu. In some embodiments, the heterogeneous catalyst incorporates Ni, Co, and Cu containing species.

The catalytically active and other species incorporated onto the substrate can be in any suitable form, including as a metal, metal oxide, metal carbonate, metal complex, metal hydride, metal nitride, metal carbide, metal hydroxide, and/or the like.

The weight ratio of Ni to each of Co (if any) and Cu (if any) independently may vary over a wide range. For instance, the weight ratio of nickel to each of Co and Cu independently may be in the range from about 1:1000 to 1000:1, preferably 1:100 to 100:1, more preferably 1:50 to 50:1. In illustrative embodiments, independently using a weight ratio of Ni to each of Cu (if any) and Co (if any) from about 3:1 to 10:1, respectively, would be suitable. These ratios are expressed on a metal basis even if the metal is incorporated into a species that includes other elemental constituents.

The total amount of catalytically active material incorporated onto the substrate may vary over a wide range. Generally, sufficient catalyst is included to facilitate carrying out the desired reductive amination. In many embodiments, the catalyst incorporates from 0.005 to 45 weight percent of catalytically active metal, desirably from 0.1 to 15 weight percent of metal. These weight percents are expressed on a metal basis even if the metal is incorporated into a species that includes other elemental constituents The amount of catalyst used in forming a cyclic polyamine using transamination is any amount, which is effective in producing the desire cyclic polyamine. For batch conditions, the quantity of catalyst may be in the range from about 0.1 to about 20 weight percent, preferably 1 to 15 weight percent, of catalyst on a metal basis per 100 parts by weight of reactant(s)

In addition to Ni, Co, and/or Cu, the heterogeneous catalyst optionally may incorporate one or more additional catalytically active species. These include Pt, Pd, or Ir, combinations of these, and the like.

The heterogeneous catalyst further includes at least one species comprising rhenium supported on the substrate. This species may be in any form such as Re metal, Re oxide, Re carbonate, Re complex, Re hydride, Re nitride, Re carbide, Re oxohydride, and/or the like. Catalysts containing Ni and Re are further described in Assignee's co-pending U.S. Published Patent Application 2010/0087682, titled "LOW METAL CATALYST COMPOSITIONS INCLUDING ACIDIC MIXED METAL OXIDE AS SUPPORT" by Stephen W. King et al. and in Assignee's co-pending U.S. Published Patent Application 2010/0137642 A1 titled "LOW METAL LOADED, ALUMINA SUPPORTED, CATALYST COMPOSITIONS AND AMINATION PROCESS" by Stephen W. King et al.

Without wishing to be bound by theory, it is believed that the Re functions at least in part as a promoter for Ni, Co, and/or Cu included on the heterogeneous catalyst, although it is possible the Re has catalytic activity as well. Accordingly, the Re is incorporated onto the catalyst in amounts effective to promote the activity of the Ni, Co, Cu and/or other catalytically active species that may be present. For reductive amination, the heterogeneous catalyst generally includes Re in higher amounts than might be used for other types of catalysis such as ethylene oxide (EO) catalysis. Thus, whereas promoting amounts of Re for ED catalysis might be in a relatively low range of 0.0001 to about 1 weight percent Re metal based on the total weight of the catalyst, a heterogeneous catalyst suitable for reductive amination generally includes at least 0.5 weight percent Re metal, preferably 1 to 15 weight percent Re based on the total weight of the catalyst.

Re has many known oxidation states including $-1$, $0$, $+1$, $+2$, $+3$, $+4$, $+5$, $+6$ and $+7$. The oxidation states $+7$, $+6$, $+4$, and $+2$ are the most common. The solubility of Re containing species in aqueous or polar organic solvents is a function of the oxidation state. Generally, solubility tends to increase with increasing oxidation state. Thus, oxides of Re with Re in the $+7$ state tend to be relatively highly soluble in aqueous media, particularly when the aqueous media is heated. In contrast, oxides of Re with Re in the $+6$, $+4$. and $+2$ states, particularly the $+4$ and $+2$ states tend to have poor solubility in aqueous media even if the media are heated.

After the heterogeneous catalyst has been reduced to give the active metal (e.g., Ni) and has been used for reductive amination in a reducing atmosphere, the Re will have been exposed to reducing conditions that act to reduce the oxidation state of the Re. Consequently, at least one species comprising Re, even substantially all of the Re, is believed to exist in lower, less soluble oxidation state(s), i.e., in an oxidation state less than $+7$, even less than $+6$, or even less than $+4$. Accordingly, such Re species have a solubility in aqueous media and/or polar organic solvents that is relatively low compared to the solubility if Re were to be in a higher oxidation state.

Conventionally, there is an expectation that using extraction to recover Re from heterogeneous catalysts, particularly using aqueous extraction, is nonselective. See U.S. Pat. No. 7,763,096 and U.S. Pat. Pub. No. 2009/0148361, U.S. Pat. No. 7,763,096 in particular reports that aqueous extraction recovers numerous other catalyst constituents along with Re. Hence, the Re is recovered in contaminated form. Surprisingly, the practice of the present invention is able to achieve more selective recovery of Re using a wide range of solvents, including aqueous extraction solvents. Without wishing to be bound, it is believed that the improved selectivity is due at least in part to having used the Re in reducing conditions prior to oxidation and extraction per below. In other words, reducing and then oxidizing the Re facilitates selective recovery via extraction. Without wishing to be bound by theory, it also is believed that these conditions are selective for Re relative to Ni, Co, and/or Cu in the context of reductive amination catalysts, whereas conventional practice had attempted Re recovery with respect to EO catalysts. EO catalysts have silver and/or other promoters which are used for EO catalysis under oxidizing, not reducing conditions. Thus, Re is not reduced to a significant extent in catalyzed EO processes.

The heterogeneous catalyst optionally may incorporate one or more additional ingredients. Examples of other ingredients include one or more additional promoters such as boron, zirconium, zinc, combinations of these, and/or the like. Examples of other promoters include one or more species including at least one of Na, Li, K, Rb, Cs, Be, Mg, Ca, Sr, Ba, Sc, Cr, Co, Mn, Y, Mb, W, V, Ta, Nb, S, P, W, Hf, Ti, combinations of these and the like. It is desirable that any additional promoter(s) used have limited solubility in the solvent used to extract the rhenium from the spent catalyst, or alternatively that the promoter(s) are easily removed from the resultant rhenium-containing admixture (e.g., by crystallization).

Re recovery is practiced after the heterogeneous catalyst has been used in a reducing atmosphere to carry out a reductive amination process. Generally, reductive amination (also known as reductive alkylation) is a form of amination that involves the conversion of a carbonyl group to an amine via an intermediate imine. Reductive amination may be direct or indirect.

At least a portion of the reductive amination occurs in a reducing atmosphere. For example, an initial part of a reductive amination may involve converting a carbonyl to an imine. This part of the reaction may or may not occur in whole or in part in a reducing atmosphere. A second part of the reaction, the imine is reduced to form an amine. This part of the reaction occurs in whole or in part in a reducing atmosphere. A reducing atmosphere is an environment that is effective to convert an imine to an amine. Exemplary reducing agents include hydrogen, metal hydrides, formic and oxalic acid, combinations of these, and/or the like.

Assignee's co-pending U.S. patent applications cited herein, each of which is incorporated herein by reference in its respective entirety for all purposes, describe technology relating to catalysts and reducing agents in the context of reductive amination.

To recover Re from the heterogeneous catalyst a liquid is selected that can function as an extraction solvent for Re-containing species in a +7 oxidation state. In this oxidation state, the Re species tends to have a solubility (a second solubility) in the liquid carrier that is greater than the solubility (first solubility) of corresponding Re-containing species in a lower oxidation state, e.g., an oxidation state less than 7+, preferably less than 6+, more preferably less than 4+. Exemplary liquids include water as well as polar organic solvents. Liquids comprising a combination of water and one or more polar organic solvents may also be used. Preferred polar organic solvents comprise oxygen and include ethers, alcohols including glycols, esters, ketones, aldehyde solvents, and combinations of these. Specific examples of preferred polar organic solvents include methanol, ethanol, isopropyl alcohol, ethylene glycol, n-butanol, i-butanol, t-butanol, allyl alcohol, hexanol, cyclopentanol, cyclohexanol, neopentyl glycol, methyl formate, methyl acetate, ethyl acetate, ethyl formate, vinyl acetate, dimethyl carbonate, ethyl lactate, ethylene carbonate, acetone, methyl ethyl ketone, ethyl isopropyl ketone, 2-pentanone, 3-pentanone, cyclopentanone, methyl vinyl ketone, acetylacetone (2,4-pentanedione), diethyl ether, diisopropyl ether, di-t-butyl ether, dimethoxyethane, furan, tetrahydrofuran, dioxane, methyl t-butyl ether, 2-methoxyethanol, 2-ethoxyethanol, diglyme, 2-butoxyethanol, combinations of these, and the like.

The preferred liquid is water. Advantageously, the present invention recovers Re selectively relative to Ni, Co, and/or Cu on reductive amination catalysts using aqueous extraction media. This is surprising in that prior investigators have reported that aqueous extraction has less selectivity for Re in other contexts such as EO catalysis. EO catalysts typically are used in oxidizing environments and for which Re must be selectively recovered relative to large amounts of Ag in many conventional modes of practice.

The liquid can be neutral, acidic, or basic. Exemplary basic solutions include aqueous NaOH, aqueous KOH, and/or aqueous ammonium hydroxide. Exemplary acidic solutions include nitric acid and/or hydrochloric acid. A relatively neutral solution is preferred to minimize the formation of rhenium salts other than the oxide(s).

The catalyst is caused to contact an oxidizing agent in order to facilitate the extraction of Re into the liquid. Oxidation causes at least a portion of the Re to be oxidized from a lower oxidation state below +7 to an oxidation state of +7. This modulates the solubility of the Re-containing species. Specifically, oxidation of the Re causes the Re to be present in a form with increased solubility in the liquid. It is believed, for example, that the oxidation provides Re+7 in the form of $Re_2O_7$ and/or $HReO_4$, which are water soluble and can be selectively extracted into aqueous media relative to other more insoluble metal(s) and metal oxide(s) that might be on the catalyst after oxidation. Without oxidation of the Re, substantially less Re can be extracted. Without having used the catalyst previously in a reducing environment, it also is believed that selectivity for Re recovery would suffer as well.

Oxidation may occur prior to and/or during the course of contact with the liquid. If oxidized prior to liquid contact, a vapor or gas phase comprising an oxidant may be caused to contact the catalyst. If oxidized at the same time as contact with the liquid, the oxidizing agent(s) may be incorporated into the liquid and/or be present in the surrounding environment.

The at least one oxidizing agent may be selected from a wide variety of options. Examples include air, air enriched with oxygen, ozone, chlorine dioxide, peroxide, nitric acid, sulfuric acid, permanganate, persulfate, combinations of these, and the like. Depending upon the manner in which the liquid contacts the catalyst, the oxidizing agent may be present in the liquid and/or in the surrounding environment. For instance, a preferred liquid with integral oxidizing power includes aqueous hydrogen peroxide and/or aqueous ozone. Where the liquid is sprayed onto the catalyst so that the catalyst is in contact with the liquid and the environment during the course of the treatment, the oxidizing agent may be present in the ambient. For instance, the oxygen in air can function as an oxidizing agent for Re if the liquid is sprayed or otherwise splashed onto the catalyst.

The strength of the oxidizing conditions can vary over a wide range. However, if the oxidizing strength is too strong, selectivity for Re may be reduced. Air in the presence of liquid water (e.g., deionized water) has suitable, mild oxidizing capabilities. Additionally, aqueous hydrogen peroxide containing 30 weight percent peroxide or less, preferably 10 weight percent or less peroxide, would be suitable.

Milder oxidation conditions cause the Re to be oxidized more slowly than if more aggressive oxidation conditions were to be used. It is believed that the mild oxidation more controllably oxidizes Re relative to other constituents of the catalyst, enhancing the selective recovery of Re relative to Ni, Co, Cu, and/or other constituents useful for reductive amination.

The liquid is caused to contact the catalyst under conditions effective to extract a Re-containing species into the liquid. Any method for establishing contact between the solvent and the catalyst can be used. Exemplary techniques include immersion, spraying, curtain coating, and rinsing for a suitable time period for a suitable number of cycles. Contact between the solvent and catalyst may be improved by including a form of agitation during the extraction process. Illustrative types of suitable agitation methods include, for example, stirring of the mixture, shaking of the mixture, spinning of the mixture, bubbling of the mixture, boiling the mixture. Other techniques involve inversion, tilting, or rotation of the mixture in an open or closed container or pan.

The oxidation and/or extraction independently or together may occur over a wide range of temperatures. In illustrative embodiments, oxidation and/or extraction independently or together may occur at a temperature in the range from 0° C. to 300° C., preferably ambient temperature to 250° C., more preferably 45° C. to 100° C. Higher temperatures are preferred so long as undue sublimation losses of Re species is avoided. The temperature refers to the temperature of the liquid at the time the liquid first contacts the catalyst.

The oxidation and/or extraction independently or together may occur over a wide range of pressures. Ambient pressure, elevated pressures, or reduced pressures may be used. In exemplary modes of practice, exemplary pressures are in a range from 0.5 atm to 10 atm, preferably 0.8 to 5 atm. Use of ambient pressure or higher are more preferred to avoid sublimation losses of Re species. Also, pressure modulation may be used to help control the liquid temperature.

The oxidation and/or extraction independently or together may occur over a wide range of time periods. If the time periods used for oxidation and/or extraction are too short, then too little Re may be recovered during each cycle of treatment. If the time period is too long, then selectivity for Re may unduly suffer. As general guidelines, time periods in the range of 1 hour to 24_hours, preferably 2 hour to 10 hours would be suitable.

Optionally, more than one cycle of oxidation and/or liquid contact may occur to enhance Re recovery.

As a consequence of the treatment, Re is recovered in the liquid extraction solvent. Due to the oxidation treatment, it is believed that at least a portion, and likely substantially all of the recovered Re is in the +7 oxidation state. The resulting liquid containing recovered Re can be thereafter used in a variety of ways. According to a preferred mode of practice, the liquid can be used as is or modified to form an impregnation solution. The impregnation solution in turn can be used to form a new heterogeneous catalyst containing the recovered Re and optionally one or more other constituents. As another option, the recovered Re can be isolated, optionally purified, and stored for future use.

The rhenium-containing admixture as obtained by the extraction process may be used as is without further processing. However, more likely, further processing may be desired to make the admixture and/or recovered Re more usable. For example, it may be preferred to concentrate the rhenium admixture. Any of the known methods for concentrating solutions may be used. A preferred method for concentrating the solution includes evaporation of a portion of the solution by, for example, heating and/or depressurization. Removal of solvent by other methods, such as selective solvent absorption or ultrafiltration methods, can also be used. It may also be preferred to remove substantially all solvent from the rhenium-containing solution to provide a solid rhenium product.

The rhenium solution may be subjected to other processing methods or chemical reactions in order to make a usable rhenium-containing end product. For example, a metal chelating agent, precipitant, polymer, or other substance may be added to the solution to cause the precipitation of, for example, a rhenium compound. The rhenium compound can be, for example, a rhenium-chelate complex, a rhenium-polymer complex, or a rhenium material, such as an oxide, sulfide, halide, or complex ion (e.g., silicate, carbonate, nitrate, tungstate) of rhenium. Alternatively, the solution can, for example, be chilled, heated, electrolyzed (e.g., to produce rhenium metal or metal alloy), allowed to stand for a period of time under specified conditions, or exposed to an oxidizing or reducing agent, as part of a process for yielding a suitable rhenium-containing end product.

The liquid admixture containing recovered Re may be used as is or as a precursor to form an impregnation solution that in turn can be used to form new catalyst. According to one option for forming a new heterogeneous catalyst useful for reductive amination, the liquid extract containing recovered Re optionally can be concentrated or otherwise treated and then combined with all or a portion of the other ingredients needed to prepare a fresh heterogeneous catalyst suitable for reductive amination. The resultant impregnation admixture can then be used to prepare the new catalyst. For this purpose, ingredients including at least one of catalytically active, Ni-containing material or precursor(s) thereof, catalytically active, Co-containing material or precursor(s) thereof, and/or catalytically active, Cu-containing material or precursor(s) thereof are incorporated into the impregnation solution prior to its use.

In other modes of practice, the liquid extract containing recovered Re optionally can be concentrated or otherwise treated and then used as an impregnation solution without adding any additional ingredients. To prepare fresh catalyst under this approach, the Re-containing impregnation solution is used in combination with one or more other sources in order to prepare the fresh catalyst. For instance, to prepare a new catalyst for use in reductive amination, the resultant catalyst may contain recovered Re, optionally additional Re from another source, and at least one of Ni, Co, and/or Cu, from another source.

Advantageously, the use of recovered Re to provide at least a portion of the Re included on a new catalyst lowers the cost of preparing the catalyst.

The rhenium-containing end product can be used to produce any other end product which requires the incorporation of rhenium. For example, the recovered rhenium can be used to treat a catalyst precursor (e.g., a catalyst support) to incorporate rhenium therein to produce a new catalyst containing rhenium that is suitable for other kinds of catalysis such as EO catalysis. The rhenium-containing liquid can also be used to make platinum-rhenium catalysts that are used in gasoline and hydrocarbon processing. The rhenium may also be used in making tungsten-rhenium alloys useful for filaments and thermocouples. The rhenium may also be used as an additive in nickel-based superalloys used in the manufacture of turbine blades and gas turbine engines. In addition, any of the known procedures of pre-deposition, co-deposition, and post-deposition of the various promoters can be used.

The present invention will now be further described with reference to the following illustrative examples.

Example 1

100 ml of distilled water was added to a round bottom flask and placed in a heating mantle. In a thimble used for a Soxhlet extractor was placed 1.0 grams of a spent reductive amination catalyst that contained 6.2 weight percent Ni and 4.8 weight percent Re supported on an alumina/silica substrate. The flask was heated to reflux open to the air in order to wash the catalyst with hot water in the presence of oxygen in the air. This extracted Re into the water. Reflux occurred for 4 hours after which the contents of the flask were allowed to cool. A 10 nil sample of the liquid was removed and replaced with 10 ml of fresh water. The flask was again heated at reflux for 4 hours to wash the catalyst and extract Re into the water. This procedure was repeated a third time. The three collected samples were analyzed by inductively coupled plasma mass spectrometry (ICP-MS) for Ni, Re, Al, and Si. The results are reported in the following table. A total of 37.4 percent of Re based on the Re contained in the spent reductive amination catalyst was recovered from the spent catalyst after 12 hours of reflux. Note that the table shows the high selectivity for recovering Re relative to Ni, Al, and Si.

| Element | 4 hours | 8 hours | 12 hours |
|---------|---------|---------|----------|
| Al | <0.1 ppm | <0.1 ppm | <0.1 ppm |
| Ni | <0.8 ppm | <0.8 ppm | <0.8 ppm |
| Re | 138 ppm | 159 ppm | 150 ppm |
| Si | 7.6 ppm | 9.3 ppm | Not measured |

Example 2

25 grams of a spent reductive amination catalyst which contained 5.0 wt. percent nickel and 5.7 wt. percent rhenium on an alumina/silica substrate was packed in a glass tube equipped with a stopcock. The spent catalyst was continually washed with about 100 ml of distilled water in the presence of air at 70° C. to 90° C. for 8 hours using a pump to recirculate the water extract through the glass tube containing the catalyst. The procedure was repeated with 100 ml of fresh distilled water six times. The aqueous extracts were combined and concentrated on a rotary evaporator to give a concentrated rhenium heptoxide/perrhenic acid solution. The Re content was measured by ICP-MS, and nickel nitrate and boric acid were added to give a catalyst impregnation solution. Using an alumina/silica substrate and procedures described in U.S. Pat. No. 6,534,441, the impregnation solution and substrate were used to prepare a heterogeneous catalyst. Note that the Re incorporated onto the substrate was in the form of recovered rhenium heptoxide/perrhenic acid in a +7 oxidation state. The performance of this catalyst was compared to an otherwise identical catalyst except that fresh perrhenic acid was used to make the comparison catalyst. The catalyst was used for the reductive amination of monoethanolamine (MEA) with ammonia. The results are provided in the table below.

| % MEA conversion | Temp, ° C. | EDA | PIP | DETA | AEEA | Others |
|---|---|---|---|---|---|---|
| Catalyst with recovered Perrhenic Acid | | | | | | |
| 30 | 157 | 67.54 | 3.25 | 12.85 | 12.41 | 3.97 |
| 40 | 163 | 64.29 | 5.16 | 14.06 | 11.10 | 5.39 |
| 50 | 169 | 60.72 | 7.70 | 14.84 | 9.87 | 6.87 |
| 60 | 174 | 56.82 | 10.86 | 15.20 | 8.73 | 8.41 |
| Catalyst with fresh Perrhenic Acid | | | | | | |
| 30 | 155 | 76.17 | 2.39 | 10.00 | 9.06 | 2.41 |
| 40 | 162 | 72.04 | 3.95 | 11.62 | 8.72 | 3.67 |
| 50 | 167 | 67.90 | 6.07 | 12.77 | 8.31 | 4.95 |
| 60 | 172 | 63.73 | 8.74 | 13.47 | 7.80 | 6.25 |

The table shows that the catalyst with recovered Re has only slightly less activity than the comparison catalyst with fresh Re. Also, even though the catalyst with recovered Re was lower in EDA selectivity, the catalyst had higher DETA selectivity than the comparison. Minor impurities in the recovered Re (e.g., Na, K, or the like) might be the reason for the differences in activity and selectivity between the two catalysts. The recovered Re solution optionally could be purified by procedures known to the skilled worker to remove these impurities.

All patents, patent applications, and publications cited herein are incorporated by reference as if individually incorporated. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for selectively recovering rhenium relative to nickel from a reductive amination catalyst, comprising the steps of:
   a) providing a heterogeneous catalyst that has been used in a reducing atmosphere to carry out a reductive amination, wherein the catalyst comprises a substrate and at least one species comprising rhenium and at least one species comprising nickel supported on the substrate, wherein the at least one species comprising rhenium has a first solubility in a liquid carrier, and wherein the substrate comprises at least 15 weight percent alumina based on the total weight of the substrate;
   b) causing the heterogeneous catalyst comprising the at least one species comprising rhenium and the at least one species comprising nickel to contact the liquid carrier in the presence of at least one oxidizing agent under conditions effective to provide a rhenium oxide that has a second solubility in the liquid carrier, wherein the second solubility is greater than the first solubility;
   c) while the liquid carrier contacts the heterogeneous catalyst comprising the at least one species comprising rhenium and the at least one species comprising nickel in step 1(b), extracting the rhenium oxide into the liquid carrier from the heterogeneous catalyst to selectively separate the rhenium oxide from the substrate relative to the at least one species comprising nickel to provide a liquid extraction solvent comprising the selectively separated rhenium oxide in the liquid carrier; and
   d) using the liquid extraction solvent to form an impregnation solution;
   e) incorporating at least one of a catalytically active, Ni-containing material, a catalytically active Co-containing material, and a catalytically active Cu-containing material into the liquid extraction solvent to provide an impregnation admixture; and
   f) using the impregnation admixture to prepare a heterogeneous catalyst.

2. The method of claim 1, wherein the substrate comprises a guest/host structure comprising a plurality of guest particles supported on a plurality of host particles, and wherein at least one species comprising rhenium and the at least one species comprising nickel are supported at least upon the guest particles.

3. The method of claim 1, wherein the substrate is calcined.

4. The method of claim 1, wherein the substrate comprises alumina and silica.

5. The method of claim 1, wherein the heterogeneous catalyst further comprises at least one of a Co-containing species and a Cu-containing species.

6. The method of claim 5, wherein the catalyst further comprises at least one Co-containing species.

7. The method of claim 5, wherein the catalyst further comprises at least one Cu-containing species.

8. The method of claim 1, wherein the at least one oxidizing agent comprises $O_2$.

9. The method of claim 1, wherein the at least one oxidizing agent comprises aqueous hydrogen peroxide.

10. The method of claim 1, wherein the heterogeneous catalyst comprises 1 to 15 weight percent Re based on the total weight of the heterogeneous catalyst.

11. The method of claim 1, wherein the catalyst provided in step (a) comprises a species comprising Re in an oxidation state in the range from −1 to +4.

12. The method of claim 1, wherein the rhenium used in step (c) comprises rhenium having an oxidation state of +7.

13. The method of claim 1, wherein the liquid carrier comprises water.

14. The method of claim 13, wherein the liquid carrier is acidic.

15. The method of claim 13, wherein the liquid carrier is basic.

16. The method of claim 13, wherein the liquid carrier is neutral.

17. The method of claim 1, wherein the liquid carrier comprises a polar organic solvent.

18. The method of claim 1, wherein step 1(b) comprises causing the catalyst comprising the at least one species comprising rhenium and the at least one species comprising nickel to contact the liquid carrier at a temperature in the range from 45° C. to 100° C.

* * * * *